(12) United States Patent
Weber

(10) Patent No.: US 8,702,651 B2
(45) Date of Patent: Apr. 22, 2014

(54) DRUG DELIVERY DEVICE WITH INSTABLE SHEATH AND/OR PUSH ELEMENT

(75) Inventor: Jan Weber, Maastricht (NL)

(73) Assignee: Boston Scientific Scimed, Inc., Maple Grove, MN (US)

( * ) Notice: Subject to any disclaimer, the term of this patent is extended or adjusted under 35 U.S.C. 154(b) by 0 days.

(21) Appl. No.: 13/489,960

(22) Filed: Jun. 6, 2012

(65) Prior Publication Data

US 2012/0316495 A1 Dec. 13, 2012

Related U.S. Application Data

(60) Provisional application No. 61/397,728, filed on Jun. 7, 2011.

(51) Int. Cl.
A61M 31/00 (2006.01)
A61M 37/00 (2006.01)
A61M 29/00 (2006.01)

(52) U.S. Cl.
USPC ............ 604/103.02; 604/103.06; 604/103.08; 604/96.01

(58) Field of Classification Search
USPC ......... 604/509, 96.01, 97.01, 101.01–101.05, 604/103.01–103.11; 623/1.11
See application file for complete search history.

(56) References Cited

U.S. PATENT DOCUMENTS

| 5,423,851 | A | 6/1995 | Samuels |
| 5,693,014 | A | 12/1997 | Abele et al. |
| 5,797,948 | A * | 8/1998 | Dunham ........................ 606/194 |
| 5,810,767 | A | 9/1998 | Klein |
| 6,533,755 | B2 * | 3/2003 | Adams ..................... 604/103.07 |
| 6,659,996 | B1 | 12/2003 | Kaldany |
| 6,939,320 | B2 | 9/2005 | Lennox |
| 7,070,613 | B2 | 7/2006 | Weber et al. |

(Continued)

FOREIGN PATENT DOCUMENTS

| EP | 1825824 A1 | 8/2007 |
| WO | 2007/096856 A2 | 8/2007 |

(Continued)

OTHER PUBLICATIONS

European Patent Office, International Search Report and Written Opinion in International Application No. PCT/US2012/036089, dated Jul. 25, 2012.

(Continued)

*Primary Examiner* — Jason Flick
*Assistant Examiner* — Rebecca E Eisenberg
(74) *Attorney, Agent, or Firm* — Kenyon & Kenyon LLP

(57) ABSTRACT

A balloon carries a drug in drug-carrying regions, wherein the drug-carrying regions protect the drug during delivery through a patient's vasculature. Once at a target site, the balloon expands, causing the drug-carrying regions to expose the drug to the target site. One drug eluting balloon device includes a longitudinal sheath that defines an interior space having a balloon disposed therein. When the balloon expands, at least one push element at least partially inverts at least one pocket formed on an outer surface of the sheath. This inversion causes a drug contained within the at least one pocket to be released to the target site. In another embodiment, a plurality of bands is provided, each band made of material having a different resistance to elongation. Upon expansion, the bands invert to expose a drug provided on a surface of the bands.

8 Claims, 6 Drawing Sheets

(56) References Cited

U.S. PATENT DOCUMENTS

| | | |
|---|---|---|
| 2011/0054396 A1 | 3/2011 | Kangas et al. |
| 2011/0054443 A1 | 3/2011 | Weber |
| 2011/0087191 A1 | 4/2011 | Scheuermann |
| 2011/0130829 A1* | 6/2011 | Clarke et al. ............... 623/1.42 |
| 2011/0152765 A1 | 6/2011 | Weber et al. |
| 2011/0301565 A1 | 12/2011 | Weber |
| 2012/0283636 A1* | 11/2012 | Rizq et al. ............... 604/103.02 |

FOREIGN PATENT DOCUMENTS

| | | |
|---|---|---|
| WO | 2009/036118 A1 | 3/2009 |
| WO | 2010/024871 A1 | 3/2010 |
| WO | 2010/080575 A2 | 7/2010 |
| WO | 2011/094476 A1 | 8/2011 |

OTHER PUBLICATIONS

European Patent Office, partial International Search Report in International Application No. PCT/US2012/041060, dated Sep. 21, 2012.

European Patent Office, International Search Report and Written Opinion in International Application No. PCT/US2012/041060, dated Nov. 15, 2012.

* cited by examiner

DRUG DELIVERY DEVICE WITH INSTABLE SHEATH AND/OR PUSH ELEMENT

CROSS REFERENCE TO RELATED APPLICATION

The present application claims priority to U.S. provisional application Ser. No. 61/397,728 filed Jun. 7, 2011, the disclosure of which is incorporated herein by reference in its entirety.

TECHNICAL FIELD

The present invention relates to medical devices, such as drug eluting balloon devices, for the delivery of medicaments to body tissue

BACKGROUND

Numerous contemporary medical procedures deliver drugs directly to target sites of diseased tissue. This targeted delivery has proven to be an advantageous approach for treating various medical conditions. Using targeted delivery, a controlled dose of the drug may be delivered directly to a target site while avoiding or minimizing exposing other parts of the body to the drug. Also, greater amounts of drug may be delivered to the afflicted parts of the body. In one approach to localized drug delivery, catheter-based, minimally invasive medical procedures are used for deploying devices such as stents, grafts, balloon catheters, and other intravascular devices.

One potential problem with these techniques is inadequate drug release (or inadequate control thereof) when the balloon is deployed. For example, in conventional drug eluting balloons, much of the drug can be lost due to washing away by the flow of blood as the balloon is being delivered to the target site.

In an effort to avoid these problems, certain drug eluting balloon systems include a sheath disposed around a balloon. One example, shown in FIGS. 5A and 5B, shows a sheath 110 provided around a balloon 120, with one or more holes 130 in sheath 110. As a gas or other working fluid is supplied through the device, balloon 120 expands. This expansion causes sheath 110 to expand as well, as shown in FIG. 5B. As sheath 110 expands, a drug provided within hole 130 is released to the target site.

These systems may have drawbacks, however. Although the shape of the hole stretches as the sheath expands, the hole itself remains relatively constant in volume. That is, the length (along the circumference of the sheath) increases as the depth of the hole decreases. As a result, less drug may be released during expansion. In some cases, as little as 10% of the drug may be released to the target site. To account for this, typical drug eluting balloons may need to include excess medicament in order to ensure that a target site receives the proper dose. In addition, these devices may have less-than-ideal control over the dosage of drug delivered to the target site.

Also, these systems may potentially lose medicament as the balloon moves through the vasculature to the target site. It can be difficult to predict the amount of medicament potentially lost as the device travels to a target site, which in turn makes it difficult to ensure that the proper amount of medicament actually reaches the target site.

Accordingly, there is a need for a drug eluting system that more effectively releases a medicament to a target site.

SUMMARY

The present invention generally relates to medical devices, specifically drug eluting balloon devices, and methods of their manufacture. In general, the various embodiments of the present invention provide a balloon carrying a drug in drug-carrying regions, wherein the drug-carrying regions protect the drug during delivery through the vasculature. Once at a target site, the balloon is expanded and the drug-carrying regions expose the drug to the target site.

In one embodiment, a drug eluting balloon device includes a longitudinal sheath that defines an interior space and has an inner surface that faces the interior space and an outer surface that faces outwardly. The device also includes a balloon disposed in the interior space of the sheath, at least one pocket formed on the outer surface of the sheath, and a medicament contained within the at least one pocket. The device includes at least one push element between the outer surface of the balloon and the pocket, the push element being located at a position opposing the at least one pocket. The push element may be formed, for example, on the inner surface of the sheath. Alternatively, the push element may be formed, for example, on the outer surface of the balloon. As the balloon expands, it forces the push element into the pocket, thereby inverting the pocket and delivering the medicament to a target site.

Another embodiment of the present invention is a drug eluting device that has a plurality of bands, each of the bands including a first stiff section and a second, more-stretchable section. The first section requires more force to elongate than the second section. The device also includes a balloon disposed in an interior space defined by the bands. A medicament is coated on at least one band on an outer surface of the second section of the band. In a first position of the device, the outer surface of the second section of each of the bands faces the interior space. In a second position of the device, at least one band inverts to expose the outer surface of the second section of the band to a target site.

The present invention also relates to methods of manufacturing drug eluting medical devices. In one embodiment, a method of manufacturing a medical device includes the steps of extruding a tube of compliant material to form a sheath that defines an interior space and has an inner surface, which faces the interior space, and an outer surface, which opposes the interior space; forming a plurality of pockets in the outer surface of the sheath; turning the sheath inside-out such that the outer surface, having the plurality of pockets thereon, faces the interior space and so that the inner surface faces outwardly; depositing a plurality drops of a material onto the inner surface of the sheath at locations opposing each of the plurality of pockets; and turning the sheath inside-out again such that the inner surface, having the plurality of drops thereon, again faces the interior space, and such that the outer surface, having the plurality of pockets thereon, again faces outwardly.

The invention may be embodied in numerous devices and through numerous methods and systems. The following detailed description, taken in conjunction with the drawings, discloses examples of the invention. Other embodiments, which incorporate some or all of the features as taught herein, are also possible.

BRIEF DESCRIPTION OF THE DRAWINGS

The present invention will become more fully understood from the following description and its accompanying drawings. These drawings are provided by way of illustration only and are not limiting of the present invention. The drawings provided with this application are as follows.

DETAILED DESCRIPTION

The present invention generally relates to drug eluting systems. The medicaments used in these systems and methods may be a broad range of therapeutic agents or drugs used in the treatment of various diseases, disorders, or other medical ailments. Throughout this description and the claims that follow, the terms "therapeutic agent," "drug," and "medicament" are used interchangeably.

The following examples are merely a few of many possible embodiments and are in no way limiting of the present invention. Similarly, the headings provided below merely aid a reader in understanding the disclosure of the present invention and in no way limit the present invention.

A. First Embodiment

Figure 1A:
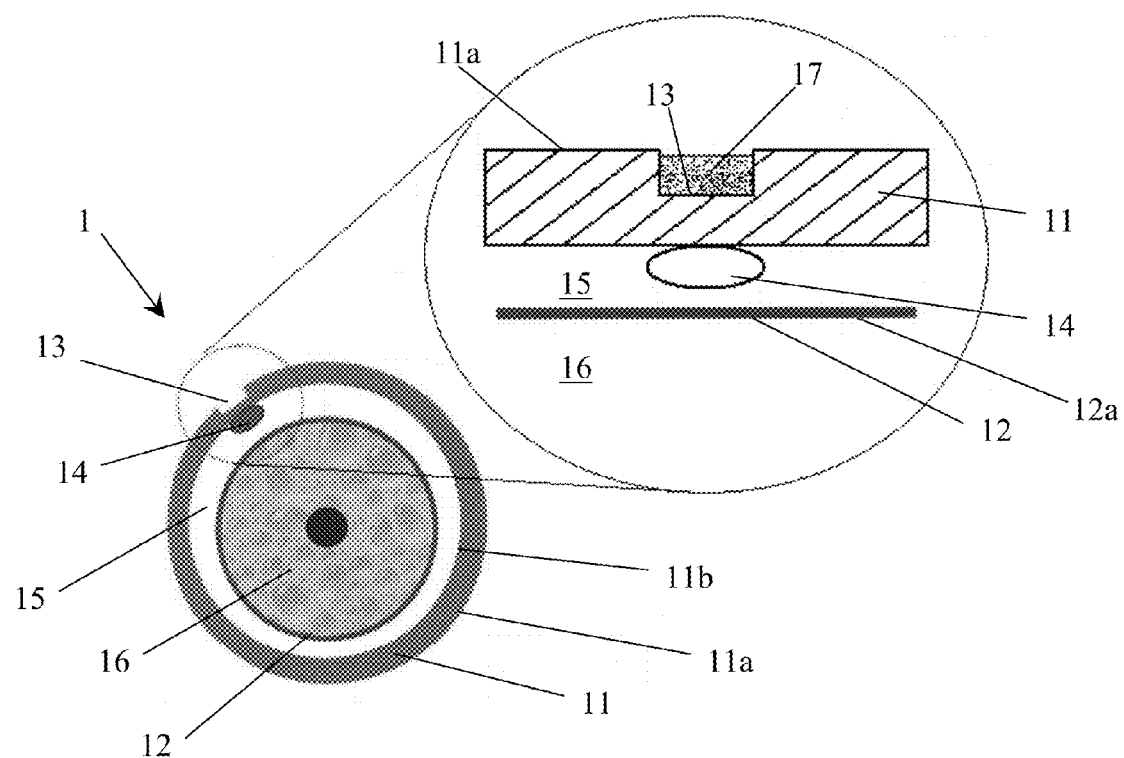
FIG. 1A shows a cross-sectional view of a drug eluting balloon device in a first position in accordance with certain embodiments of the present invention.
Figure 1B:
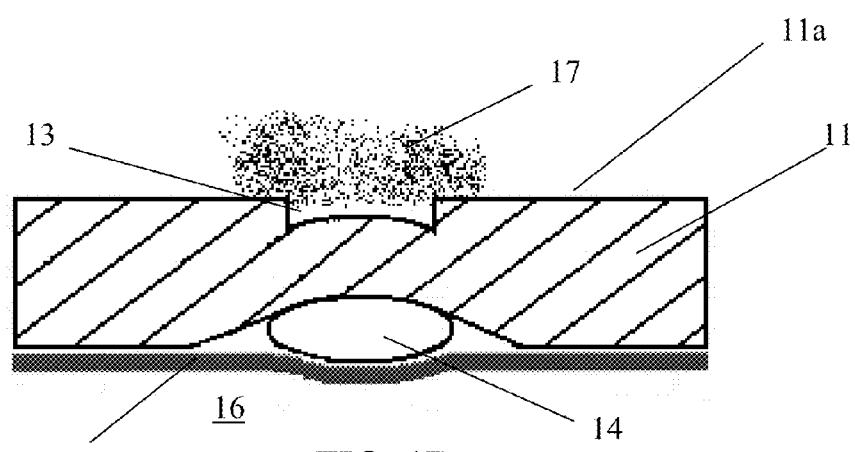
FIG. 1B shows an enlarged view of a portion of the device of FIG. 1A in a second position.

One example of a drug eluting balloon device in accordance with certain embodiments of the present invention is shown in FIGS. 1A and 1B. This drug eluting balloon device 1 includes a sheath 11, a balloon 12, at least one pocket 13 formed on an outer surface of sheath 11, and at least one push element 14 located between the outer surface of the balloon and the pocket. In this illustrated embodiment, the push element(s) is/are formed on an inner surface of sheath 11. Alternatively, the push element(s) may be formed on the outer surface of the balloon.

Sheath 11 is generally in the shape of a tube (extending circumferentially and longitudinally) and defines an interior space 15. Sheath 11 includes an outer surface 11a and an inner surface 11b. Inner surface 11b faces interior space 15, while outer surface 11a opposes interior space 15.

The sheath may be open-ended or closed-ended. Also, the sheath is preferably made of a compliant material, such as a relatively compliant polyurethane, silicone, or TECOTHANE® (produced by The Lubrizol Corporation). By "relatively compliant," it is meant that the material is compliant enough such that it can displace when pushed upon by the stiffer material of push element 14.

Sheath 11 has a circular cross-section. However, this need not be the case for all embodiments. Sheaths of other embodiments may have cross-sections of varying shapes, as needed for a particular application.

Sheath 11 includes at least one pocket 13 formed on its outer face 11a. Preferably, sheath 11 includes a plurality of pockets spaced both radially and longitudinally along outer surface 11a of the sheath. These pockets may vary in shape and depth and are preferably sized to accommodate at least one medicament 17. Medicament 17 may be a broad range of drugs or other therapeutic agents to be delivered to a target site. In certain embodiments, the target site may be within the vasculature (such as within an artery) of a human or other mammalian body.

Figure 1C:
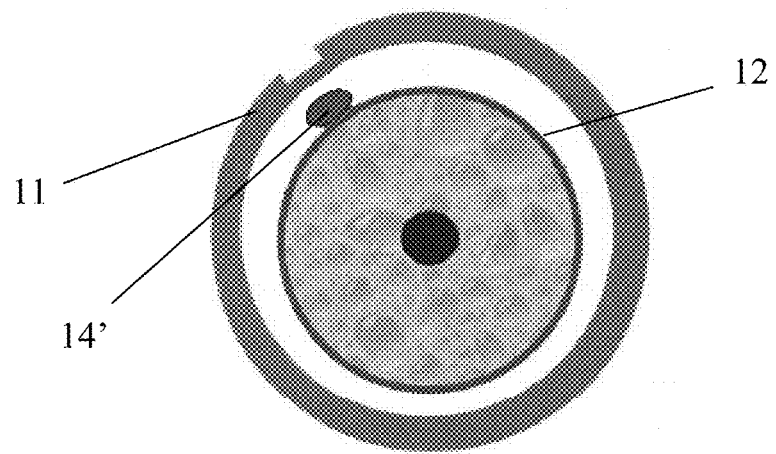
FIG. 1C shows an alternative embodiment of the device shown in FIG. 1A, in which a push element is located on an outer surface of a balloon.

Inner surface 11b of sheath 11 includes at least one push element 14 thereon. (Alternatively, at least one push element 14' (or all push elements) may be located on the outer surface of balloon 12, as shown in FIG. 1C.) Preferably, sheath 11 includes a plurality of push elements spaced both radially and longitudinally along inner surface 11b of sheath 11. Preferably, a push element 14 is formed at each position that corresponds to the position of a pocket 13 on outer surface 11a. That is, push elements 14 are preferably located directly underneath (or opposing) pockets 13, as shown in FIG. 1A. Each pocket preferably has a push element on an opposing surface of the sheath.

Push elements 14 may be sized to approximately match the circumferential width and/or longitudinal length of pockets 13. In other embodiments, however, push elements 14 may have dimensions that are larger or smaller than the dimensions of their corresponding pockets.

Push elements 14 may be made of a glue, such as cyanoacrylate or polyurethane. In certain embodiments, push elements 14 are drops of glue integrally formed with or bonded to inner surface 11b of sheath 11. The push elements may be formed of, for example, an epoxy with a cured durometer hardness of D85 and a nominal viscosity of approximately 110,000 cP (such as product number DYMAX 8-20626 available from Dynmax Corporation) or a bit softer cyano acrylate, a light curable adhesive. In other embodiments, additional particles may be mixed in with the glue to form push elements 14. The addition of these particles hardens the glue in cases where the glue material itself is too soft to suitably push the compliant material of sheath 11. (In other words, the added particles make the push elements stiffer, aiding in their ability to push medicament out of pocket 13.) Suitable added particles include powder-like materials such as sand or silicone. Additional, non-limiting examples of hard particles that may be embedded within the glue drops include polystyrene or polymethyl meta acrylate (PMMA) spheres. In one specific embodiment, the push elements may be formed of a light curable glue embedded with 100 μm PMMA spheres.

Interior space 15 of sheath 11 is sized to accommodate balloon 12 therein. In this embodiment, balloon 12 is expandable. That is, when a gas or other fluid is fed through an interior space 16, balloon 12 expands as a result of internal pressure forces acting on the balloon's inner surface. In this embodiment, balloon 12 is preferably made from a non-compliant material such as a relatively non-compliant polyurethane or nylon. By "relatively non-compliant," it is meant that the material is stiff enough such that it can displace the softer, compliant material of sheath 11.

Balloon 12 is preferably an elongated shape capable of radial expansion. The balloon may be of a folded type, or it may be non-folded.

Balloon 12 is configured to be expandable from a first position (shown in FIG. 1A) to a second position (a portion of which is shown in FIG. 1B). In the first position, balloon 12 is unexpanded. In the second position, balloon 12 is at least partially expanded. In this position, gas or another working fluid has been forced into interior space 16, thereby providing an internal pressure that causes balloon 12 to expand radially.

In the second position, outer surface 12a of balloon 12 contacts and pushes against push element 14 as shown in FIG. 1B. The internal pressure in interior space 16 forces push element 14 radially outward. This in turn forces the interior of pocket 13 outward, thereby forcing medicament 17 out of pocket 13 to the target site. That is, the expansion of balloon 12 forces push element 14 into a portion of the compliant material of sheath 11, thereby causing pocket 13 to at least partially invert, displacing medicament 17 to a target site. Also in this position, a portion of outer surface 12a may contact a portion of inner surface 11b of sheath 11.

In an example embodiment, the pockets may be configured to release drug crystals of a size between 1 and 10 μm. In one example, about 2 μg of medicament is released per square millimeter. The depth of the pockets may be, for example, between 25 and 100 μm, with the pockets covering approximately 2-8% of the device's surface area. The depth of the pockets may also be, for example, between 50% and 75% of the sheath's thickness. The diameter of the pockets may be, for example, on the order of 100 μm to 1 mm. In the case of non-circular pockets, similar dimension may be used such that the pocket's surface area is equivalent to that described for circular pockets.

One example of a balloon used in accordance with certain embodiments of the present invention may have a diameter of 3.5 mm, a length of 16 mm, and a surface area of 154 mm$^2$. Pockets used with this example may be round holes having a depth of 50 μm and a diameter of 200 μm. For a 4% coverage of the device's surface area, approximately 200 pockets may be used. Other dimensions and numbers of pockets are of course possible.

A sheath used in conjunction with this 16 mm balloon may have, for example, an outer diameter of approximately 1.1 mm, a wall thickness of approximately 100 μm, and a length of approximately 22 mm.

The push element may be the same size as, larger than, or smaller than the pockets. For example, in certain embodiments, the diameter of a push element may be twice that of the pocket. In other embodiments, the push element diameter is equal to that of the pocket.

Preferably, sheath 11 is made of a compliant material, while balloon 12 is made of a non-compliant material. In a modified example of this embodiment, however, the sheath may be made from a non-compliant material, while the balloon may be made from a compliant material. In this modified example, shown in FIGS. 2A and 2B, a sheath 21 preferably includes a plurality of open areas 25, such that it resembles a braided structure common to some stents. In one particular example, sheath 21 is formed of nylon strips 29 having a width of approximately 1 mm. Pockets 23 may be drilled into the surface of strips 29. Alternatively, the pockets may be formed by an excimer ablation laser.

Figure 2A:
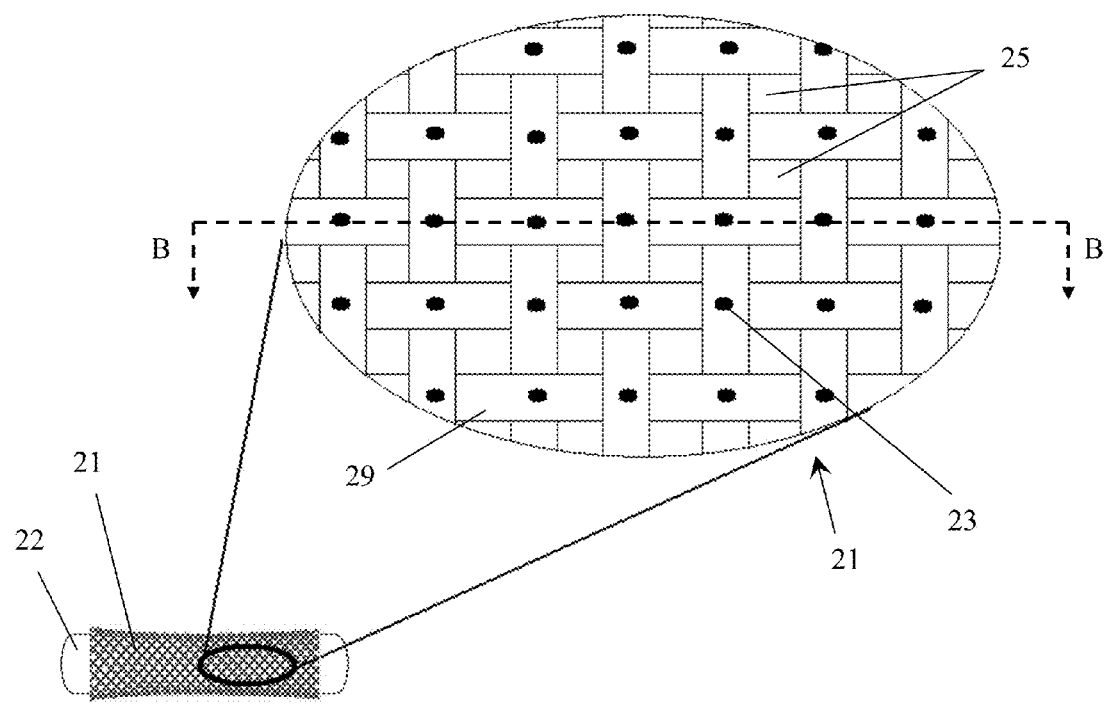
FIG. 2A shows an enhanced top view of a drug eluting balloon device in a first position in accordance with certain other embodiments of the present invention.
Figure 2B:
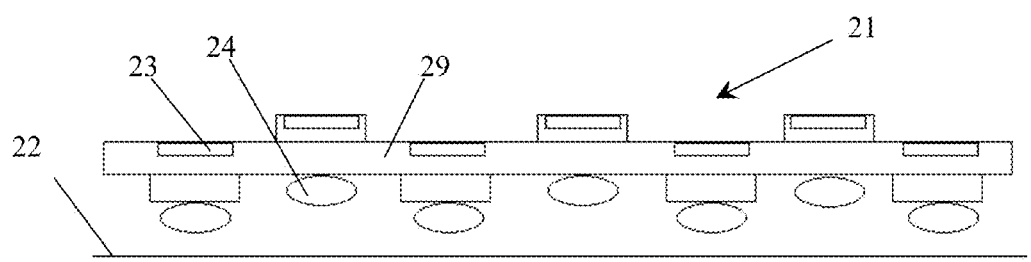
FIG. 2B shows a cross-sectional side view of the device of FIG. 2A.

As shown in FIG. 2B, which is a cross-sectional side view along line B-B in FIG. 2A, the inner surface of sheath 21 includes at least one push element 24 (and preferably a plurality of push elements). The outer surface of sheath 21 includes at least one pocket 23 (and preferably a plurality of pockets). Similar to pocket 13 and push element 14 previously described, pockets 23 at least partially invert or turn inside-out when pressed by push elements 24 as balloon 22 expands. The inversion of the pockets displaces a medicament, contained within the pockets, to a target site.

Alternatively, a portion of the balloon's outer surface could be coated with a medicament such that, in the second position, the portions of the balloon coated with the medicament protrude through the open areas in the non-compliant sheath to contact the target site. Preferably, a balloon used in this case would be non-folded.

An example process of manufacturing an example device within the first embodiment is as follows. First, a tube of compliant material is extruded to form a sheath. Next, a plurality of pockets is formed in the exposed surface of the sheath using a laser, drill, or other known means. Then, the sheath is inverted such that the previously exposed surface (containing the pockets thereon) becomes an inner surface. After inverting the sheath, drops of glue material are deposited onto the now-exposed surface of the sheath at locations corresponding to each pocket. This material forms the push elements. After forming the push elements, the sheath is inverted once again so that the surface containing the pockets thereon now faces outward. The sheath is then placed on the balloon, and therapeutic agent is loaded into the pockets.

B. Second Embodiment

Figure 3A:
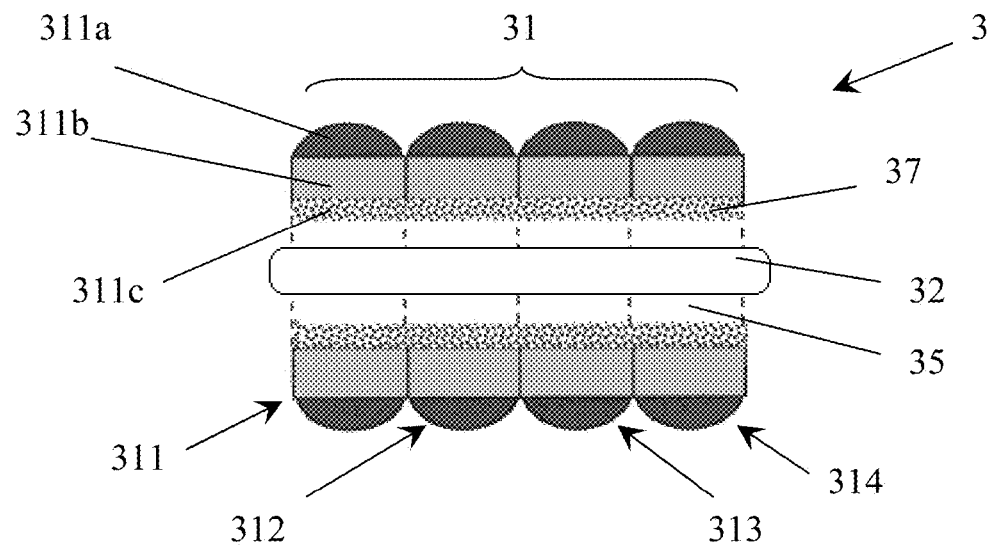
FIG. 3A shows a side sectional view of a drug eluting device in a first position in accordance with still other embodiments of the present invention.
Figure 3B:
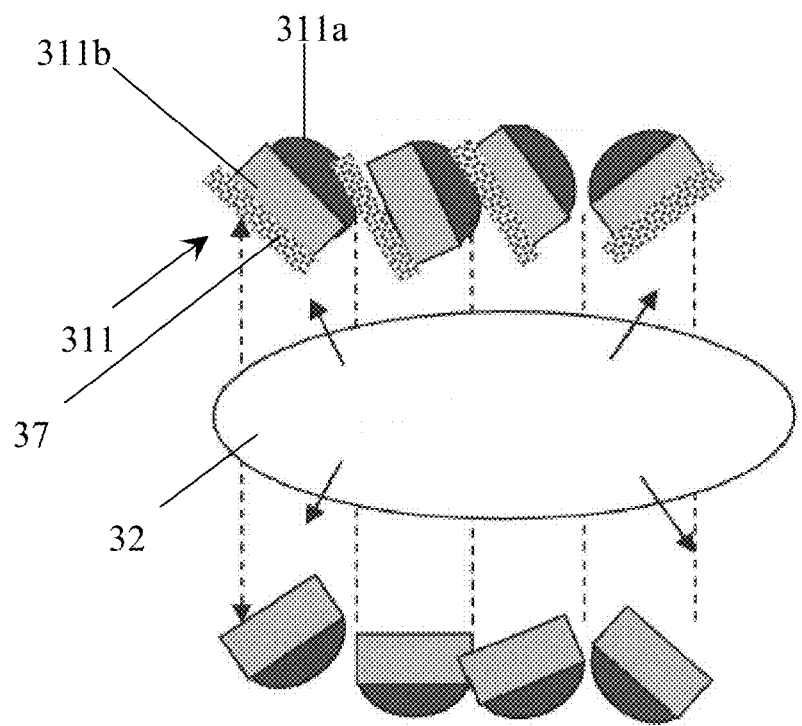
FIG. 3B shows the device of FIG. 3A in a position between first and second positions.
Figure 3C:
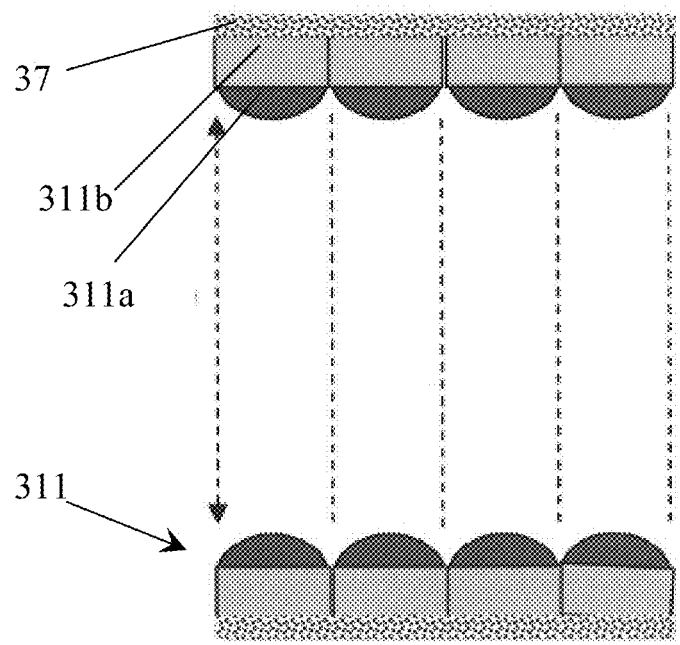
FIG. 3C shows the device of FIGS. 3A and 3B in a second position.

Another example of a drug eluting balloon device in accordance with certain other embodiments of the present invention is shown in FIGS. 3A-3C. Referring to FIG. 3A, this device 3 includes a plurality of bands 31 that defines an interior space 35 and a balloon 32 disposed within interior space 35.

This example employs the principle of bistability in order to deliver a medicament to a target site. Bistability is a naturally-occurring phenomenon. Typically, a bistable system is at rest in two states, which need not be symmetric with respect to stored energy. A defining characteristic of bistability is simply that two stable states are separated by a peak. The application of this principle to certain embodiments of the present invention will be more particularly understood upon reviewing the following description.

Elastic bands 311, 312, 313, 314 (collectively, bands 31) are placed along the length of balloon 32. Bands 31 may be ring-like structures, similar to typical rubber bands in general shape and function (but not necessarily size). In one particular example, the bands each have a length of approximately 0.5 mm.

Each band has a first section (such as section 311a), which is stiff. The first section faces outwardly in a first position of device 3. Each band also includes a second section (such as section 311b), which is more easily stretched than the first section. The second section faces interior space 35 in the first position. In order to ensure that the bands do not shift off of the device, the outermost bands may be made from a single, compliant material. That is, the distal-most and proximal-most bands would be made of a single, compliant material. Because these bands are not bistable, they would not flip during expansion of the balloon, thereby ensuring that none of the inner bands slide or shift off the device.

At least one second section 311b (and preferably each of the second sections) includes a medicament coated on an outer surface 311c of second section 311b. To facilitate delivery of medicament 37, and to prevent medicament 37 from completely rubbing off on balloon 32, outer surface 311c of second section 311b may be a rough surface. This allows medicament to accumulate in the tiny orifices created by the rough surface, thereby preventing at least some of the medicament from being exposed to the balloon during expansion. Alternatively, pockets or potholes may be formed on the outer surface of the second section to accommodate the medicament.

Balloon 32 is disposed in interior space 35 defined by bands 31. That is, balloon 32 is contained within (or surrounded by) the plurality of bands 31. Balloon 32 is preferably an elongated shape capable of radial expansion.

At least one (and preferably each) first section of bands 31 is made from a material that requires more force to elongate than the material of the second sections. That is, the first sections are stiffer than the second sections. This makes bands 31 bistable. That is, when balloon 32 expands, each band will tend to "flip" (or invert) due to the relative differences in the resistance to stretching. More particularly, in the first position of the device, shown in FIG. 3A, the second sections of bands 31 face interior space 35, while the first sections face outward toward a potential target site. Non-limiting examples of suitable materials for construction of the first sections include nylon and a relatively hard polyurethane. Non-limiting examples of suitable materials for the second sections include softer polyurethanes such as silicone, or TECOTHANE® (produced by The Lubrizol Corporation). Any material is suitable such that the first section requires more force to elongate than the second section.

In the first position of device 3, shown in FIG. 3A, bands 31 are arranged such that their second sections (such as section 311b) face interior space 35. Also, the first sections (such as section 311a) face outward in the first position.

As gas or another working fluid is provided to device 3, balloon 32 expands as shown in FIG. 3B. This expansion causes bands 31 to elongate in order to accommodate the increased balloon diameter. Because the first sections do not elongate as easily as the second sections, the second sections will more easily elongate to a larger circumference. This difference causes the bands to rotate. That is, in accordance with the principles of bistability, bands 31 will tend to flip, such that the second sections now face outward, while the first sections face interior space 35. The rounded shape (shown in FIGS. 3A-3C) of the outer surface of the first sections (such as section 311a) facilitates the inversion of bands 31. The first sections need not have a rounded shape, however.

FIG. 3C depicts device 3 in a second position. (In FIG. 3C, balloon 32 has been removed for clarity.) In this position, bands 31 have flipped such that the positions of the first and second sections relative to a target site have reversed. In this position, medicament 37 contacts the target site. Thus, in the second position of device 3, bands 31 have switched such that medicament 37 is exposed to the target site. In the second position, the outer surface of balloon 32 may be in direct contact with the first sections of bands 31.

Figure 4A:
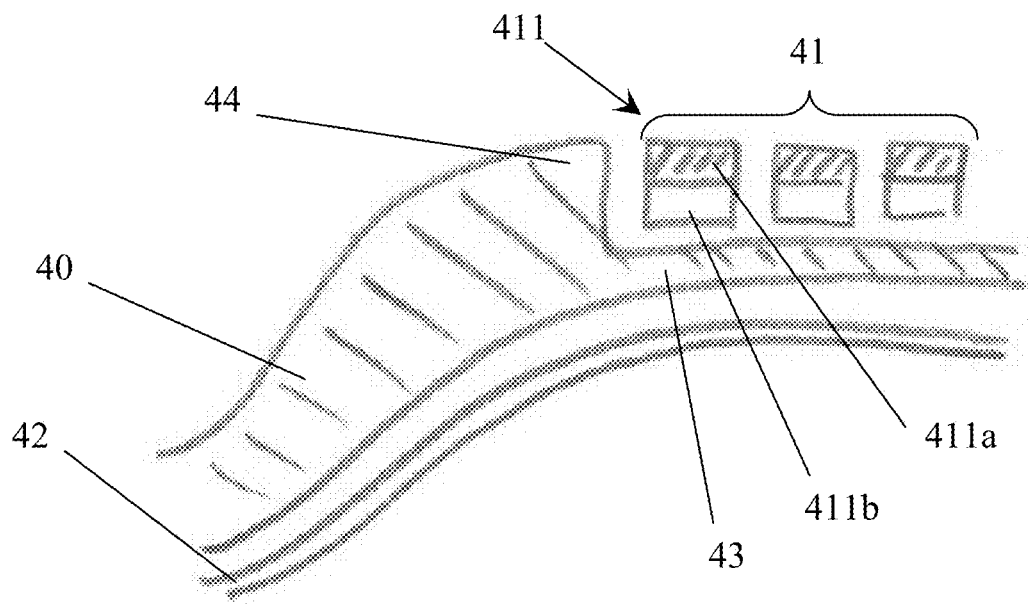
FIG. 4A shows a side sectional view of a portion of a drug eluting device in an unexpanded position in accordance with still other embodiments of the present invention.
Figure 4B:
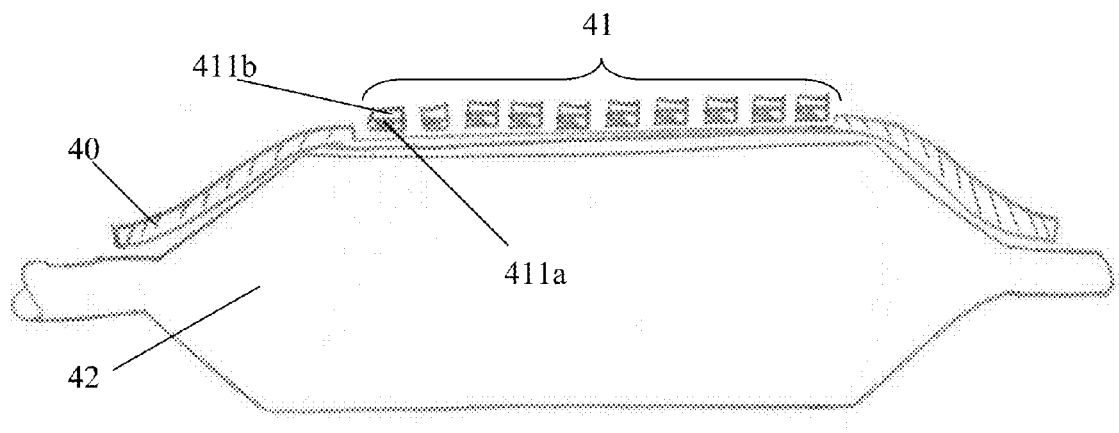
FIG. 4B shows a side sectional view of the device of FIG. 4A in an expanded position.
Figure 5A:
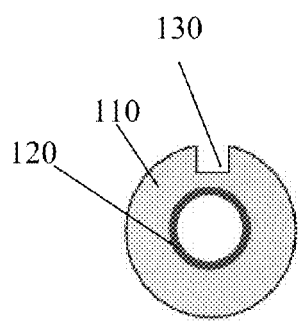
FIG. 5A shows a cross-sectional view of one example of a prior art drug eluting balloon device in an unexpanded position.
Figure 5B:
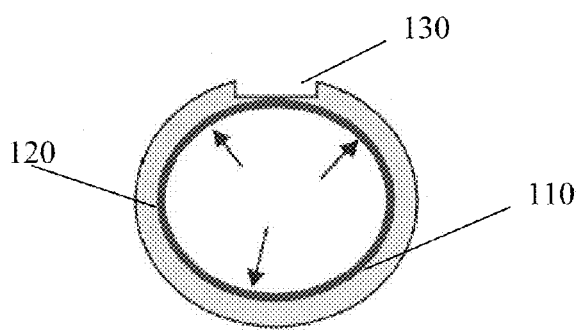
FIG. 5B shows the device of FIG. 5A in an expanded position.

A modified example of this embodiment is shown in FIGS. 4A and 4B. This modified example includes a balloon 42 disposed within a longitudinal elastic sheath 40. Sheath 40 includes a thin central portion 43, which is a recessed portion along the outer circumference of sheath 40. Thin portion 43 defines a pocket or recess into which a plurality of bands 41 is disposed. The size of the pocket formed in the sheath can range up to 80% (or more) of the sheath's diameter.

At least one band 411 (and preferably each band) includes a first section (such as section 411a), which is stiff, and a second section (such as section 411b), which is more easily stretched than the first section. Similar to bands 31 described previously, one or more of bands 41 may be bistable.

In a first position of this device, in which balloon 42 is unexpanded, bands 41 are disposed at least partially within the recess formed by thin portion 43 of sheath 40. Preferably, bands 41 are completely contained within the recess formed by thin portion 43 such that a thick portion 44 of sheath 40 extends further radially than bands 41. This ensures that bands 41 do not flip or otherwise displace as the device moves within a patient toward a target site.

As balloon 42 expands to the second position, the bistable bands 41 flip, exposing the outer surface of the second sections (such as section 411b) to a target site, as shown in FIG. 4B. This exposes a medicament, provided on the outer surface of the second sections, to the target site. In the second position, at least a portion of bands 41 protrude beyond the outer diameter of sheath 40 to provide medicament to a target site.

Rather than using a sheath, the modified example can instead include a so-called "dog-bone shaped" balloon that has a profile forming a pocket to receive the plurality of bands. As with the sheath described previously, the size of the pocket formed in the balloon can range up to 80% (or more) of the balloon's total diameter.

Non-limiting examples of suitable compliant materials include polymeric materials such as polyamide, thermoplastic polyamide, polyesters, polyphenylene sulfides, polyethylene terephthalate, HDPE or Pebax. Other non-limiting examples include elastic materials such as silicone rubber or latex.

The devices and methods disclosed herein may be used in conjunction with a broad variety of medicaments to treat various diseases or medical conditions. Preferred, non-limiting examples of suitable medicaments include paclitaxel, everolimus, zotarolimus, biolimus, or other drugs that reduce restenosis. Other non-limiting examples of therapeutic agents used in conjunction with the present invention include the therapeutic agents identified in U.S. Pat. No. 7,070,613 (issued Jul. 4, 2006, to Weber, et al.) and in U.S. Patent Application Publication No. 2011/0054443 (published Mar. 3, 2011), each of which is incorporated herein by reference.

I claim:

1. A drug eluting balloon device, comprising:
a plurality of bands, each of the bands including a first section and a second section, wherein the first section requires more force to elongate than the second section;
a balloon disposed in an interior space defined by the plurality of bands; and
a medicament coated on at least one band of the plurality of bands on an outer surface of the second section of the at least one band,
wherein, in a first position of the device, the outer surface of the second section of each of the plurality of bands faces the interior space, and
wherein, in a second position of the device, the at least one band of the plurality of bands rotates to expose the outer surface of the second section of the at least one band to a target site.

2. The device of claim 1, wherein the first section of each of the plurality of bands is made from a material firmer than that of the second sections.

3. The device of claim 1, wherein the balloon is at least partially expanded in the second position of the device.

4. The device of claim 1, wherein each of the plurality of bands has a ring-like shape.

5. The device of claim 1, wherein at least one band of the plurality of bands is made from a compliant material.

6. The device of claim 5, wherein the compliant material is selected from the group consisting of silicone and a relatively soft polyurethane.

7. The device of claim 1, further comprising a longitudinal sheath provided outside of the balloon, the sheath including a thin portion on which the plurality of bands is at least partially disposed.

8. The device of claim 7, wherein the plurality of bands is fully disposed on the thin portion of the sheath.

\* \* \* \* \*